United States Patent [19]
Stearns et al.

[11] Patent Number: 5,262,840
[45] Date of Patent: Nov. 16, 1993

[54] MULTISPECTRAL REFLECTOMETER

[75] Inventors: Thornton Stearns; Subhash C. Sarkar, both of Amherst, N.H.

[73] Assignee: Sequa Corporation, New York, N.Y.

[21] Appl. No.: 781

[22] Filed: Jan. 4, 1993

Related U.S. Application Data

[63] Continuation of Ser. No. 472,591, Jan. 30, 1990, abandoned.

[51] Int. Cl.$^5$ .............................. G01J 3/18; G01J 3/04
[52] U.S. Cl. ...................................... 356/328; 356/334
[58] Field of Search ............... 356/307, 319, 324, 326, 356/328, 331–334; 385/121

[56] References Cited

U.S. PATENT DOCUMENTS

| | | | |
|---|---|---|---|
| 3,885,879 | 5/1975 | Louder et al. | 356/326 |
| 4,285,596 | 8/1981 | Landa | 356/328 |
| 4,449,821 | 5/1984 | Lee | 356/319 |
| 4,756,619 | 7/1988 | Gerlinger et al. | 356/446 X |
| 4,810,089 | 3/1989 | Murakoshi et al. | 356/365 X |
| 4,815,849 | 3/1989 | Sullivan | 356/328 |
| 4,836,674 | 6/1989 | Lequime et al. | 356/328 |
| 4,886,355 | 12/1989 | Keane | 356/328 |
| 4,936,684 | 6/1990 | Keane | 356/328 |
| 5,040,889 | 8/1991 | Keane | 356/328 |
| 5,042,893 | 8/1991 | Ong | 385/121 X |

FOREIGN PATENT DOCUMENTS

0315939A2 11/1988 European Pat. Off. .

OTHER PUBLICATIONS

Clinical Chemistry, vol. 34, No. 11, Nov. 1988, pp. 2367–2370; W. E. Neeley: "A reflectance photometer with a Square photodiode array detector for use on multilayer dry-film slides".
J. M. Lerner, "Diffraction Gratings Ruled and Holographic—A Review," SPIE vol. 240, 1980.

Primary Examiner—Vincent P. McGraw
Assistant Examiner—K. P. Hantis
Attorney, Agent, or Firm—Mitchell D. Bittman; Peter J. Manus

[57] ABSTRACT

A reflectometer for measuring absorption of light in selected regions of the light spectrum by a diffuse reflector. The reflectometer is adapted to precisely measure absorption resulting from the constituents present in body fluids. The sample to be measured is illuminated by a focused light source at an angle of 45° to its surface. The light diffusely reflected about the normal to the sample falls on a small round bundle of optical fibers At the opposite end of the bundle, the fibers are arranged into a narrow rectangle. This rectangle forms the entrance slit for a concave holographic diffraction grating. The grating forms images of this entrance slit spectrally separated over a flat field suitable for recording the spectrum on film or on an array of discrete detectors.

14 Claims, 12 Drawing Sheets

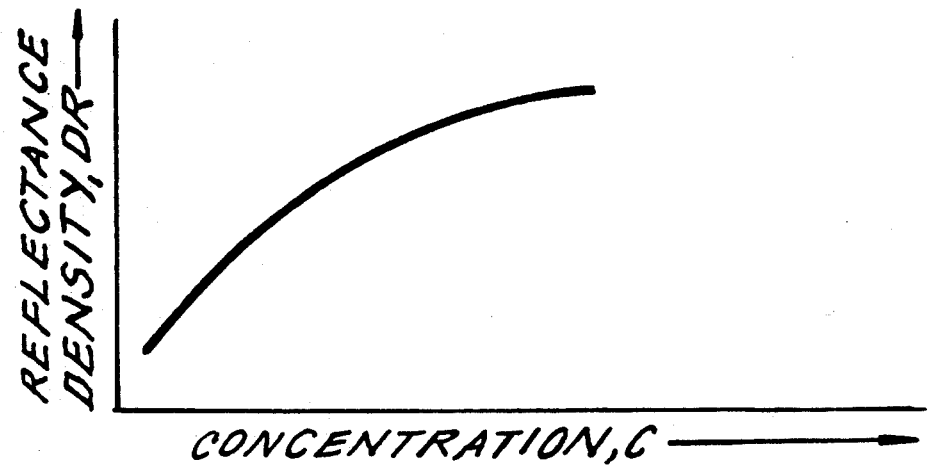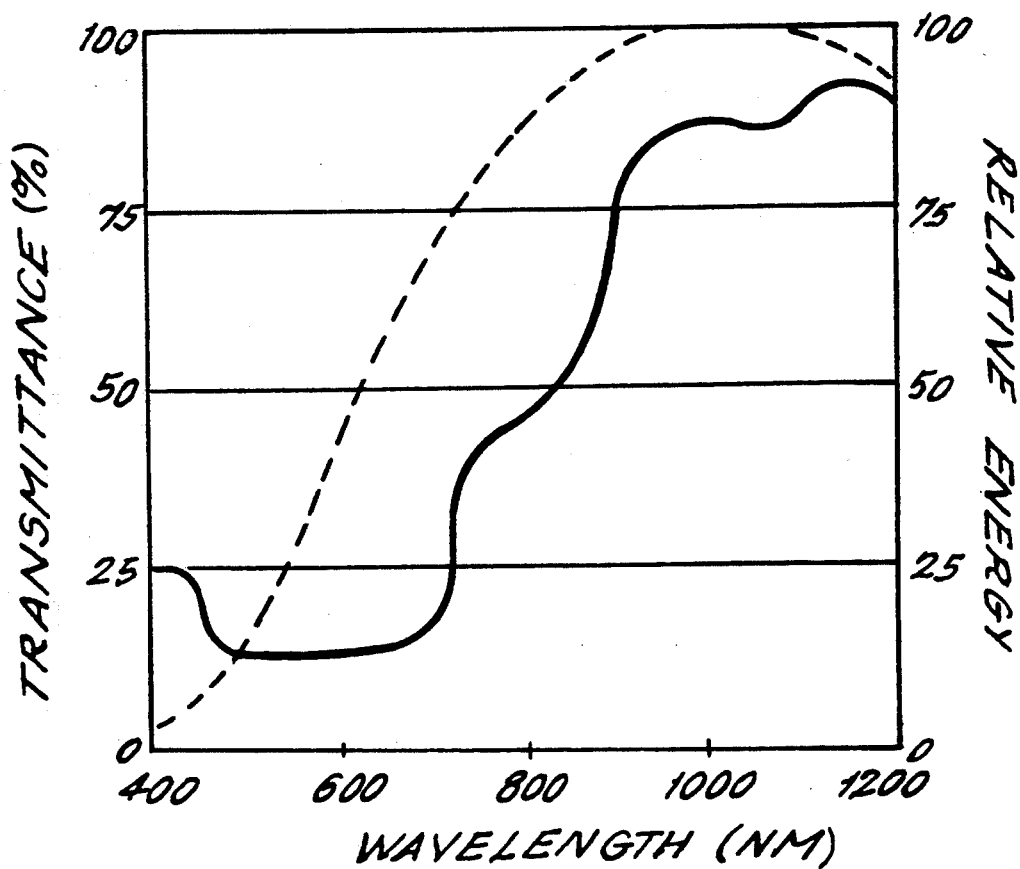

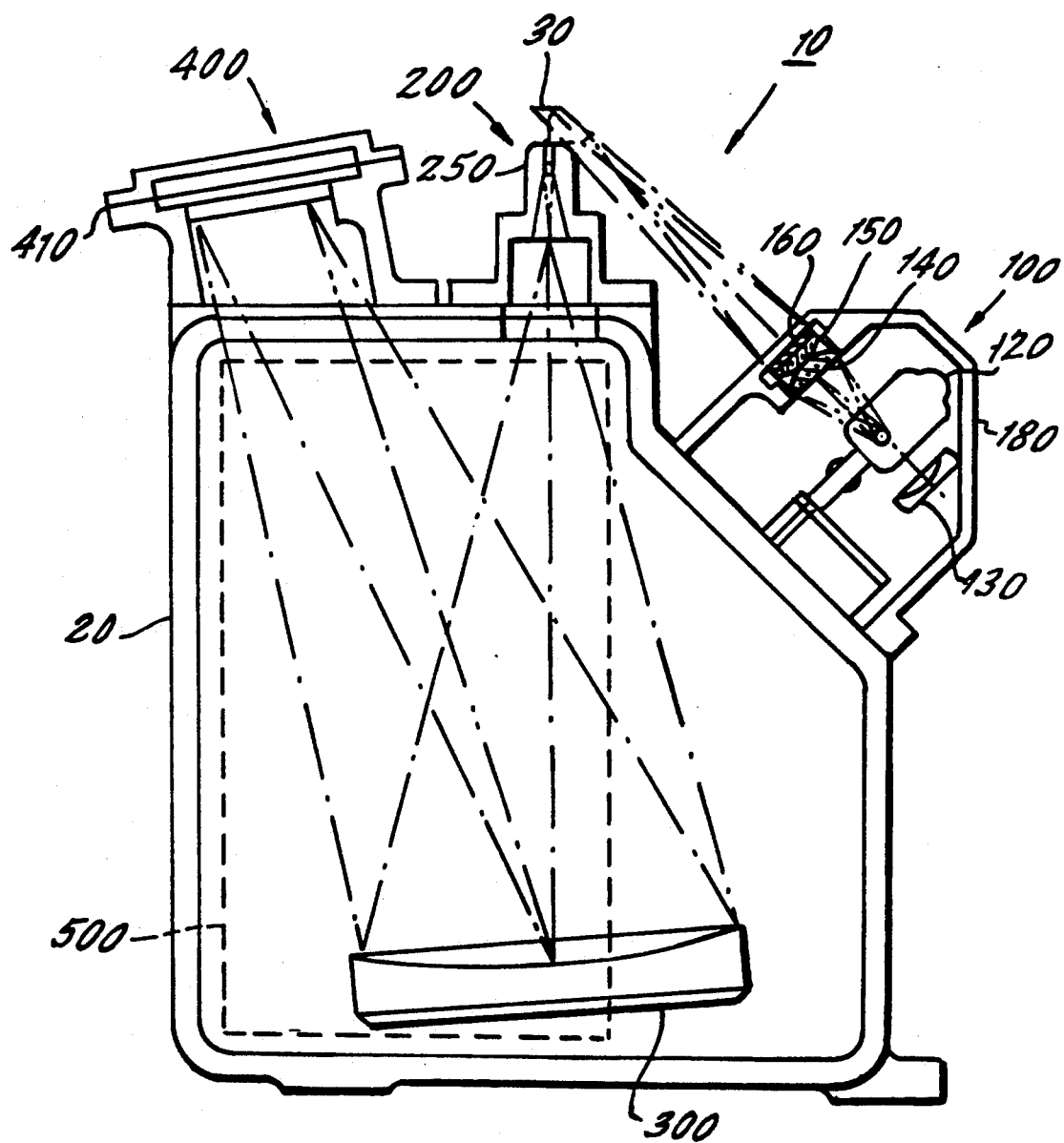

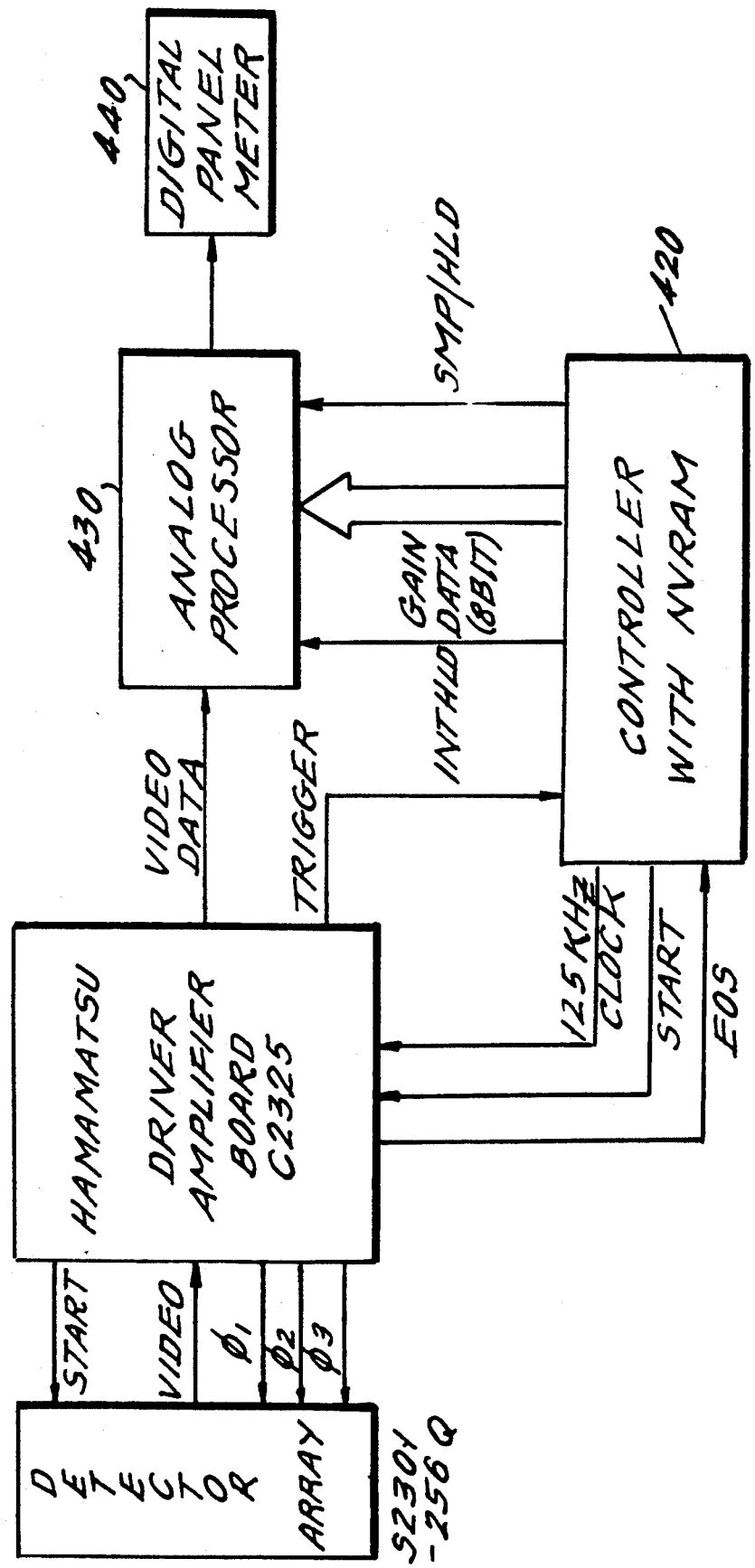

MULTISPECTRAL REFLECTOMETER

This application is a continuation of application Ser. No. 07/472,591, now abandoned, filed Jan. 30, 1990.

BACKGROUND OF THE INVENTION

1. Field of the Invention

The present invention relates to a system for measuring the absorption of light in selected regions of the light spectrum by a diffuse reflector, and more specifically, to a reflectometer utilizing a holographic grating and a photodetector array.

2. Description of the Related Art

There exists a nonlinear but deterministic relationship between the negative log of diffused reflectance (Reflectance density $D_R$) at specific wavelengths from a sample containing an absorbing analyte and the concentration, C of the analyte in the sample as shown below:

$$(D_R = -\log R)$$

and $$D_R = f(C)$$

A typical $D_R$ vs. concentration curve is shown in FIG. 1.

By measuring the diffused reflected energy from a given sample at a specific wavelength one can, therefore, estimate the concentration of the absorbing analyte present in the same if an a-priori knowledge of the function f(C) exists at the given wavelength. The $D_R$ vs. C curves are usually established with standard solutions of known concentrations of the analyte.

The wavelength band is analyte-specific and is selected on the basis of constituent molecules of the analyte solutions. The wavelength bands are often experimentally determined from the absorption spectrum and picked up at the highest change of slope.

SUMMARY OF THE INVENTION

The object of the present invention is to provide a compact instrument capable of accurately measuring the diffusely reflected energy from a given sample at specific wavelength across a wavelength band.

The foregoing objective is achieved by providing multispectral reflectometer having the following five major components:

1. An illumination system that illuminates a defined area of the sample the reflectance of which at a given wavelength is to be measured
2. A fiber-optics collection system which collects the reflected energy from the sample and forms a rectangular entrance slit for the concave grating at the other end.
3. A holographically recorded concave grating that accepts the reflected energy from the slide transmitted by the entrance slit of the fiberoptic bundle and then disperses it into its component wavelengths on a flat plane of spectrum.
4. A photodetector array located at the spectral plane that detects the diffracted energy at each wavelength.
5. Electronic circuitry that processes the photocurrent generated by the photodetectors at various wavelengths and converts it into numerical data that corresponds to the reflectance value within a given wavelength bandwidth.

Preferably, the illumination system consists of a halogen lamp, a spherical mirror (preferably a dichroic spherical mirror) positioned behind the lamp and a pair of lenses and a heat filter positioned in front of the lamp. The lenses focus a spot of light from the lamp onto a sample slide.

Although the reflectometer of the present invention has been developed primarily for colorimetric measurements, it will find a wide variety of applications in the field of immunossay measurements including fluorometry with slight modifications i.e., by filtering the illumination system to obtain specific fluorescent exitation wavelengths for the analyte being measured. Since the reflectometer measures the reflectance at various wavelengths, typically from 340 nm to 700 nm, it will also be well suited for lab/research instruments to identify appropriate absorption wavelength band, or conversely, identify the presence/absence of specific compounds in a given sample.

BRIEF DESCRIPTION OF THE DRAWINGS

Other features and advantages of the present invention will become apparent when the following description is read in conjunction with the accompanying drawings, in which:

FIG. 1 shows a graph of the reflectance density $(D_R)$ versus analyte concentration for a typical analyte.

FIG. 2 shows a side view of the reflectometer of the invention.

FIG. 8 shows the angles of reflection as the image is reflected from the entrance slit to the photodetector array by the grating.

FIG. 9 is a block diagram of the electronic circuitry for controlling the photodetector array and processing signals received from the array.

DETAILED DESCRIPTION OF THE PREFERRED EMBODIMENTS

Figure 5:
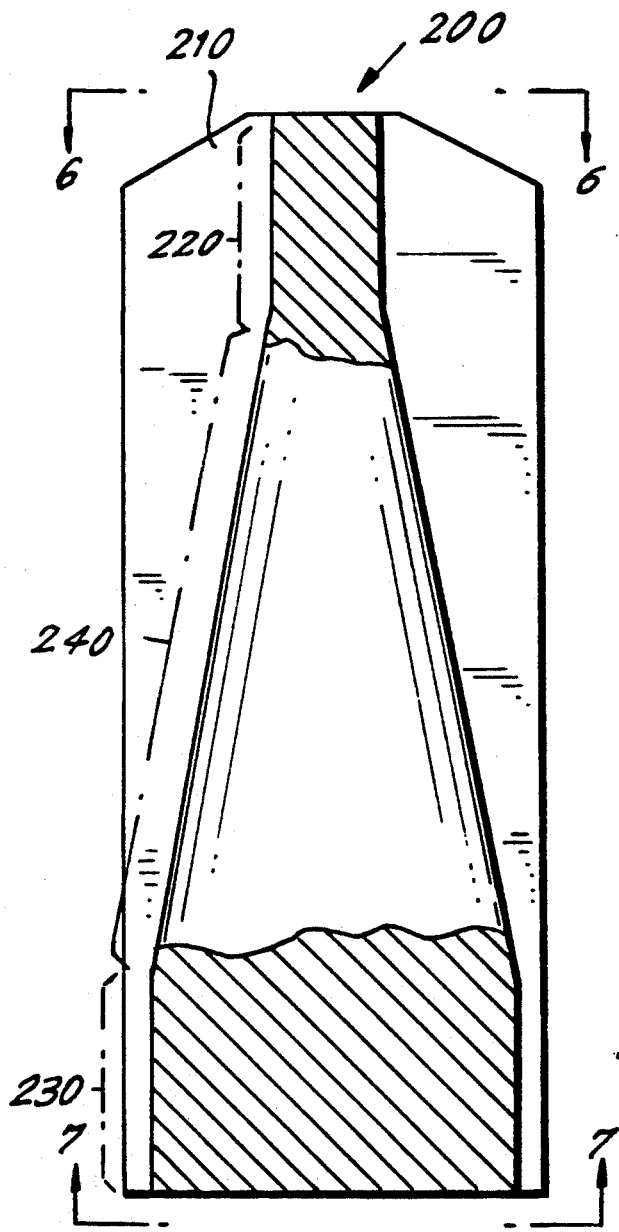
FIG. 5 is a side view of the fiber optic collector of the system.

Referring first to FIG. 2, the reflectometer of the invention, identified generally by reference numeral 10, has five primary components: an illumination system 100; a fiber optics collection system 200; a holographic concave grating 300; a photodetector array 400; and electronic processing circuitry (not shown)

Illumination system 100 is positioned on housing 20 such that a sample 30 (preferably contained in a slide) is irradiated Diffused, reflected light energy from sample 30 is collected by fiber optics collection system 200, which forms the collected energy into the shape of a rectangular slit and directs it onto diffraction grating 300. The grating 300 disperses the reflected energy into its component wavelengths onto a flat plane of spectrum. Photodetector array 400 is located at the spectral plane and detects the reflected energy at each wavelength. Electronic circuitry (described later) processes the photocurrent generated by photodetector array 400 at various wavelengths and converts it into numerical data that corresponds to the reflectance value within a given wavelength bandwidth.

The individual components of the invention will now be described in greater detail Illumination system 100 includes a lamp 120, a spherical concave dichroic mirror 130, and a pair of lenses 140, 150, all of which are mounted in a housing 160. Lamp 120 is used as a light source. A spherical concave, mirror 130 (preferably dichroic) is located behind lamp 120 in order that the lenses obtain light from the back as well as the front of the lamp. The combination of the direct and reflected light from the lamp is focussed by the lens system which can have a ratio of focal length to diameter (f#) of about 0.6 to 1.0. In the illustrated embodiment, two lenses 140 and 150 are located in front of lamp 120 and have a f# of about 1.0 and the mirror 130 is a concave mirror having a center of curvature concentric with the lamp. Lamp radiation was projected onto the sample 30 in a 4 mm diameter sample area.

Lamp 120 is preferably a miniature halogen lamp such as a Gilway L7394 (6 V, 20 W) lamp, which has a 2000 hour lifetime at a color temperature of 3,000° K. and has filament dimensions of 2.9 mms (length) by 1.2 mms (diameter). The lamp is mounted in suitable ceramic socket (such as a Gilway H9941 socket) and assembled in a wand with a bayonet pin for easily removal/replacement.

Figure 3:
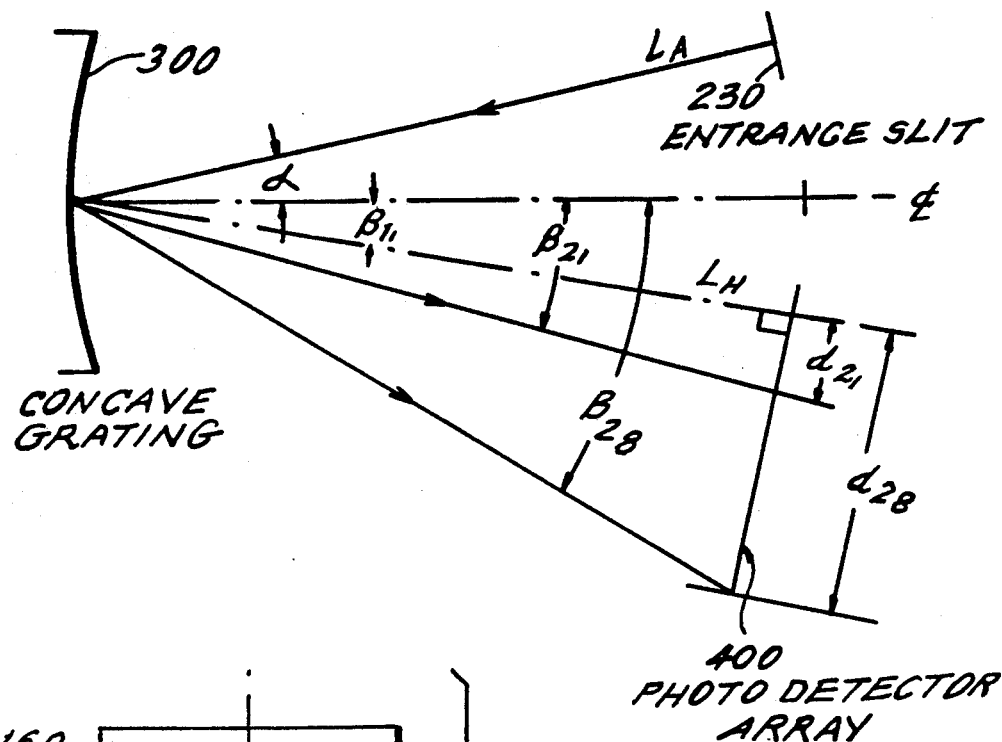
FIG. 3 shows the spectral energy distribution of a lamp and a dichroic mirror which may be utilized in the system.

Concave mirror 130 is preferably a 10 dichroic, spherical mirror with a 25 mm radius. The spectral energy distributions of the preferred lamp and a dichroic mirror (also available from Gilway) are shown in FIG. 3.

Figure 4:
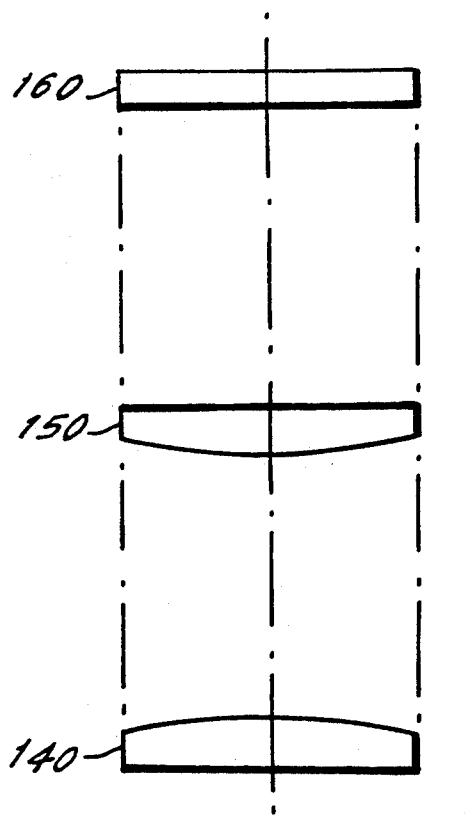
FIG. 4 is an exploded view of the lens and heat filter arrangement of the system.

An exploded view of the lens and heat filter arrangement is shown in FIG. 4. Heat filter 160 is a Schott BG 40, silicon dioxide coated filter.

Sample 30 is ordinarily contained in a conventional slide (not shown). The slide may be loaded manually into a view port (not shown) located above collector 200 which collects the diffused, reflected radiation from sample 30 Illumination system 100 irradiates about a 4 mm diameter area of the sample (at the center). The angle of incidence of the light on the slide should not be included within the acceptance angle of the fiber optics bundle In the embodiment illustrated, the angle is 45°.

Figure 15:
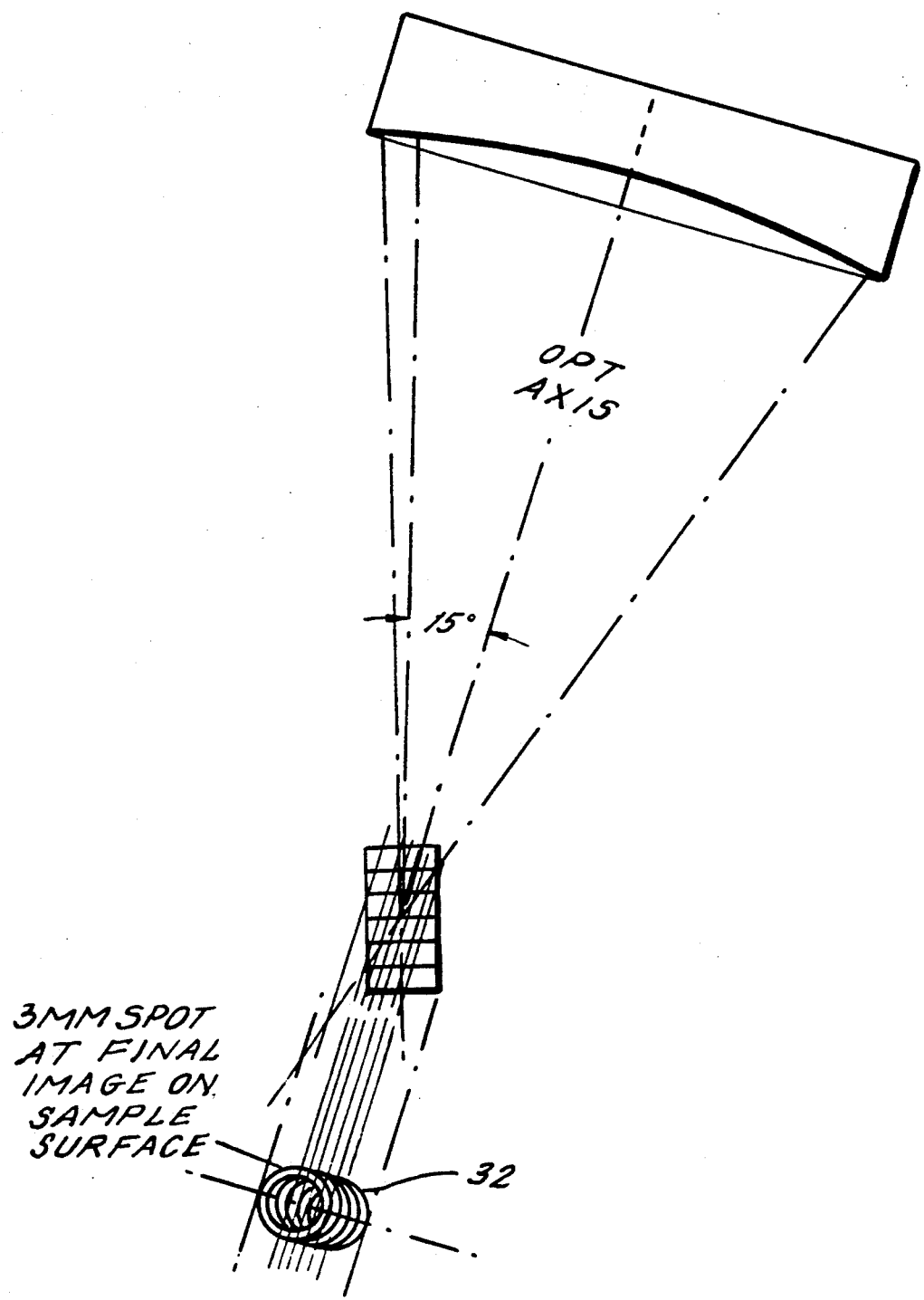
FIG. 15 and 16 show the optical path of light focussed onto a sample.
Figure 16:
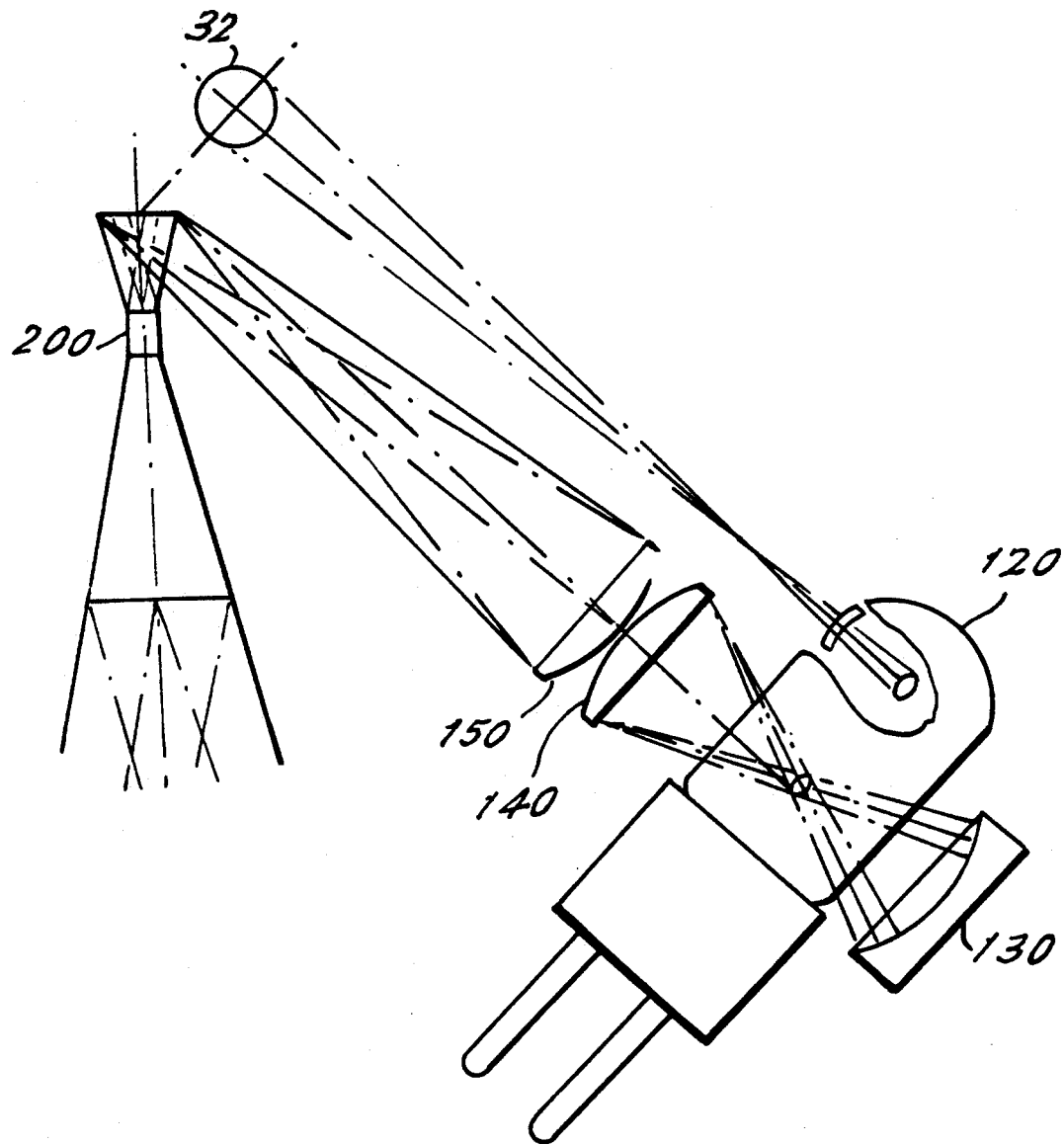

The mode by which light from lamp 120 is focused on sample 30 in a cool and efficient manner will now be described in connection with FIGS. 15 and 16. With a filament coil axis oriented at 15° to the optical axis, the image 32 produced appears to fill a 45° ellipse having dimensions 3 mm by 2.1 mm. The reflection of the image is distorted into a frustum of a cone in which the end coils are 2 mm and 2.2 mm in diameter, respectively. The focussing lens assembly 140 and 150 increases this distortion by about 50% and also softens the focus by aberration on the sample surface, as shown in FIG. 15, to produce a 3 mm round spot at the final image which is seen at 45°.

The light diffusely reflected from the sample 30 is collected by collector 200. Collector 200 is preferably a fiber optic bundle mounted in a housing 250. Collector 200 must collect as much light energy as can be transmitted through the slit dimension to flood (fill) the full surface of the concave grating 300 which will be described below For this to be realized, each fiber must see and transmit light from a source that subtends an equal or larger solid angle than does the grating facing the other end of the fibers. The acceptance capability of the fibers, i.e., the numerical aperture, is preferably one and one half to two times as large as the system requires It remains only therefore to place the fibers close enough to the source so that each fiber delivers light to the whole area of the grating Any over-filling of the grating should be blocked off or absorbed to reduce scattered light in the system.

Figure 6:
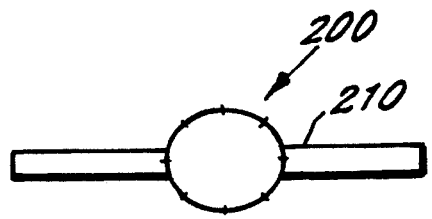
FIG. 6 is an end view of the collector along lines 6—6 of FIG. 5.
Figure 7:
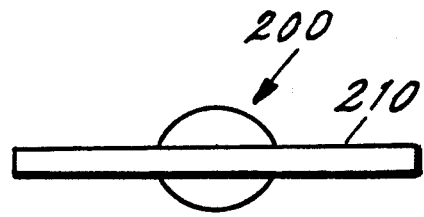
FIG. 7 is an end view of the collector along lines 7—7 of FIG. 5.

A suitable fiber optic collector is illustrated in FIG. 5-7. It comprises a bored airtight housing 210. Within end portions 220 and 230, the fibers are held rigidly in place by epoxy, while the fibers in center portion 240 remain flexible (i.e., not secured). End 220, having a circular cross-section as better seen in FIG. 6, is used to collect the reflected energy from illuminated sample 30. End 230, having a rectangular cross-section as seen in end view FIG. 7, serves as an entrance slit to concave grating 300. The collector 200 may contain 250 optical fibers, each fiber having a 50 micron diameter and a 0.6 NA. At end 230, the fibers are arranged in preferably at least two, and in the preferred embodiment five, rows of 50 fibers to form the shape of a rectangular slit.

A key element of the system is the grating. By its concave spherical shape, it performs the vital function of imaging reflected energy projected onto it through the slit end 230 of collector 200 onto an array of detectors, i.e., it disperses the energy into its component wavelengths on a flat plane of spectrum This imaging function typically has two serious drawbacks, curvature of the spectral image surface on the Rowland circle, a circle whose diameter is equal to the radius of the grating, and aberrations of the slit image, mainly astigmatism. The process of making the ruled or replicated concave grating is also subject to two faults, scattered light from irregularities of the groove texture and ghosts from cyclical spacing variations.

A holographically recorded diffraction grating is not produced by mechanical means, but by the three-dimensional interference pattern set up by two laser beams which becomes the surface of the grating by subsequent developing and aluminum coating. This process produces a grating with a flat spectrum over a limited but adequate range of wavelengths and dispersion. The principal aberration, astigmatism, is reduced by an order of magnitude, scattering is significantly reduced and ghosts are eliminated. These types of gratings are discussed in Lerner et al., "Diffraction Gratings Ruled and Holographic—A Review", SPIE vol. 240, Periodic Structures, Gratings, Moire Patterns and Diffraction Phenomena (1980), herein incorporated by reference.

The holographically recorded grating (HRD) suitable for the present invention preferably has 200 to 600 grooves/mm with an outside diameter of 40 to 200 mm. An acceptable grating having 310 grooves/mm, an outside diameter of 50 mm and a 100 mm radius curvature is available from Instruments S.A. Another suitable grating available from Instruments S.A. has 320 grooves, an outside diameter of 28 mm and a 40 mm radius of curvature. The specific spectral line locations from the zero order image are calculated from the basic grating equation of first order:

$$\sin \alpha + \sin \beta = n\lambda = 310 \times 10^{-3}\lambda$$

where n is number of grooves per micron and λ is the wavelength in microns and the angles are as shown in FIG. 8. Referring to FIG. 8, which shows the grating angles for grating 300:

$$\beta = \sin^{-1}(n\lambda + \sin \alpha)$$

and dispersion is given by $$\frac{\Delta\lambda}{\Delta d_\lambda} = \frac{1}{n \cdot L_H} \cdot \cos\beta_\lambda \cdot \cos^2(\beta_\lambda - \beta_H)$$

Calculated locations of the spectral lines for the preferred grating with 310 grooves/mm are shown in Table I below:

TABLE I

| | Wavelength channels and their locations (from zero order image) | | |
|---|---|---|---|
| Channel # | Wavelength range nm | Distance range mm | Dispersion nm/mm |
| 1 | 327 to 353 | 11.046 to 11.920 | 29.7 |
| 2* | 393 to 407 | 13.272 to 13.747 | 29.5 |
| 3** | 433 to 439 | 14.624 to 14.829 | 29.3 |
| 4 | 449 to 471 | 15.177 to 14.829 | 29.2 |
| 5 | 495 to 505 | 16.756 to 17.100 | 29.1 |
| 6* | 530 to 550 | 17.965 to 18.660 | 28.8 |
| 7 | 594 to 606 | 20.199 to 20.622 | 28.4 |
| 8 | 624 to 636 | 21.257 to 21.682 | 28.2 |
| 9 | 666 to 674 | 22.750 to 23.036 | 28.0 |
| 10 | 674 to 686 | 23.036 to 23.466 | 27.9 |

**Primary wavelength calibration channel from low pressure mercury lamp
*Secondary wavelength calibration channel from low pressure mercury lamp Photodetector array 400 is positioned at the spectral plane upon which the grating 300 disperses the diffusely reflected energy from sample 30. Detector array 400 may be mounted in a sub-housing 410 attached to housing 20 by any suitable means.

Figure 10:
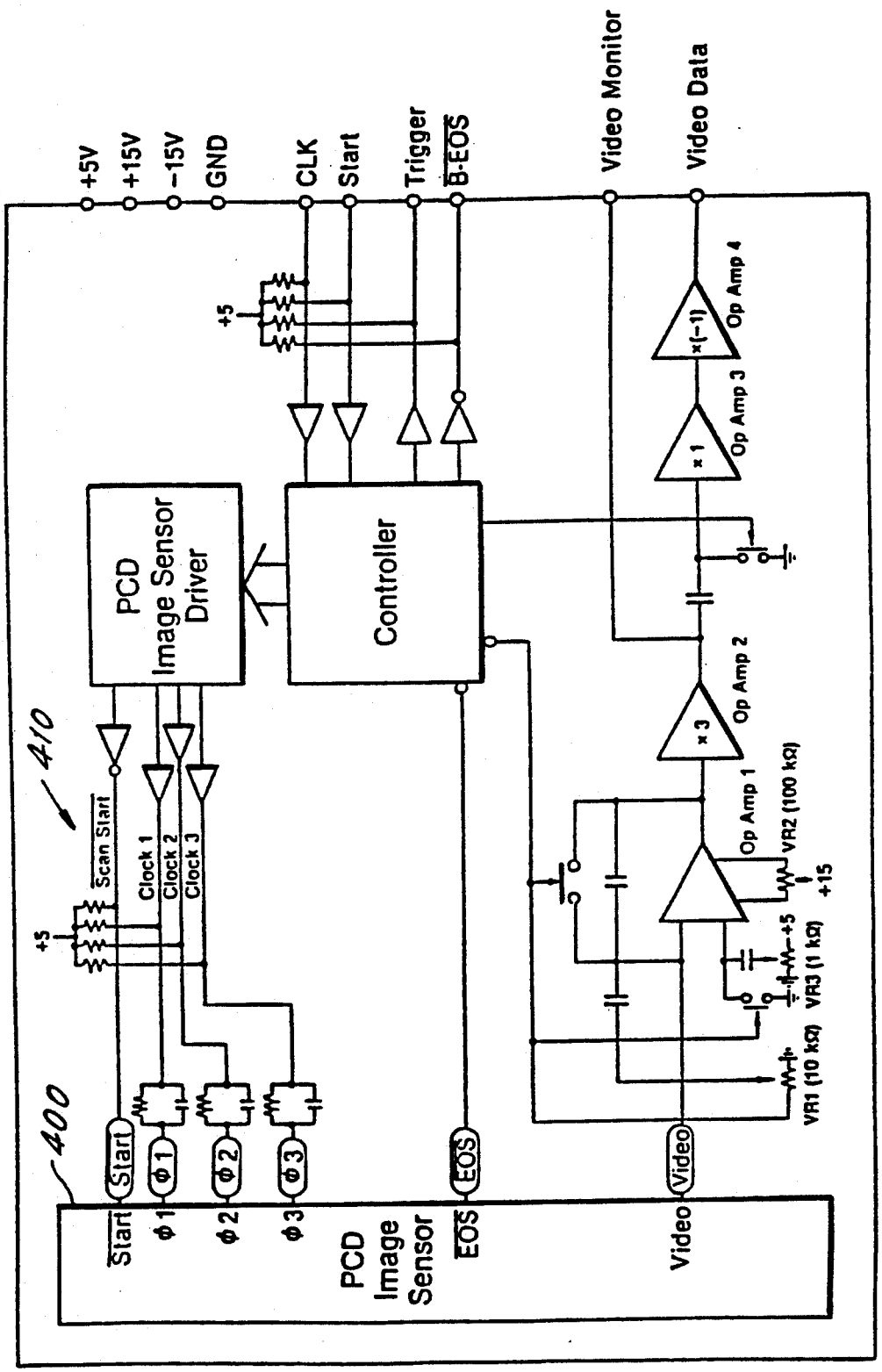
FIG. 10 is a schematic block diagram of the detector array driver/amplifier.

Detector array 400 can be a 256 element PCD linear image sensor from HAMAMATSU (S2301-256Q). In such a detector array, each photodiode element is 36 microns×2.5 mm with 50 micron pitch. Saturation exposure for each element is around 100 pJ. The maximum integration time is calculated to be around 6 ms to produce the saturation charge of 20 pC. The noise is estimated to be about $1 \times 10^{-3}$ pC. (rms) at 70° F. The detector dynamic range is therefore 86 dB. In addition, the detector has a considerable dark output which is temperature and storage time dependent. With 10 ms integration time at 70° F., the dark output is about 0.13 pC. This output can, however, be offset at the amplifier with a temperature tracking circuit. FIG. 9 shows a block diagram of the electronic circuitry for driving and processing the signal from detector array 400, and FIG. 10 is a more detailed block diagram of the driver-/amplifier board 410.

Figure 11:
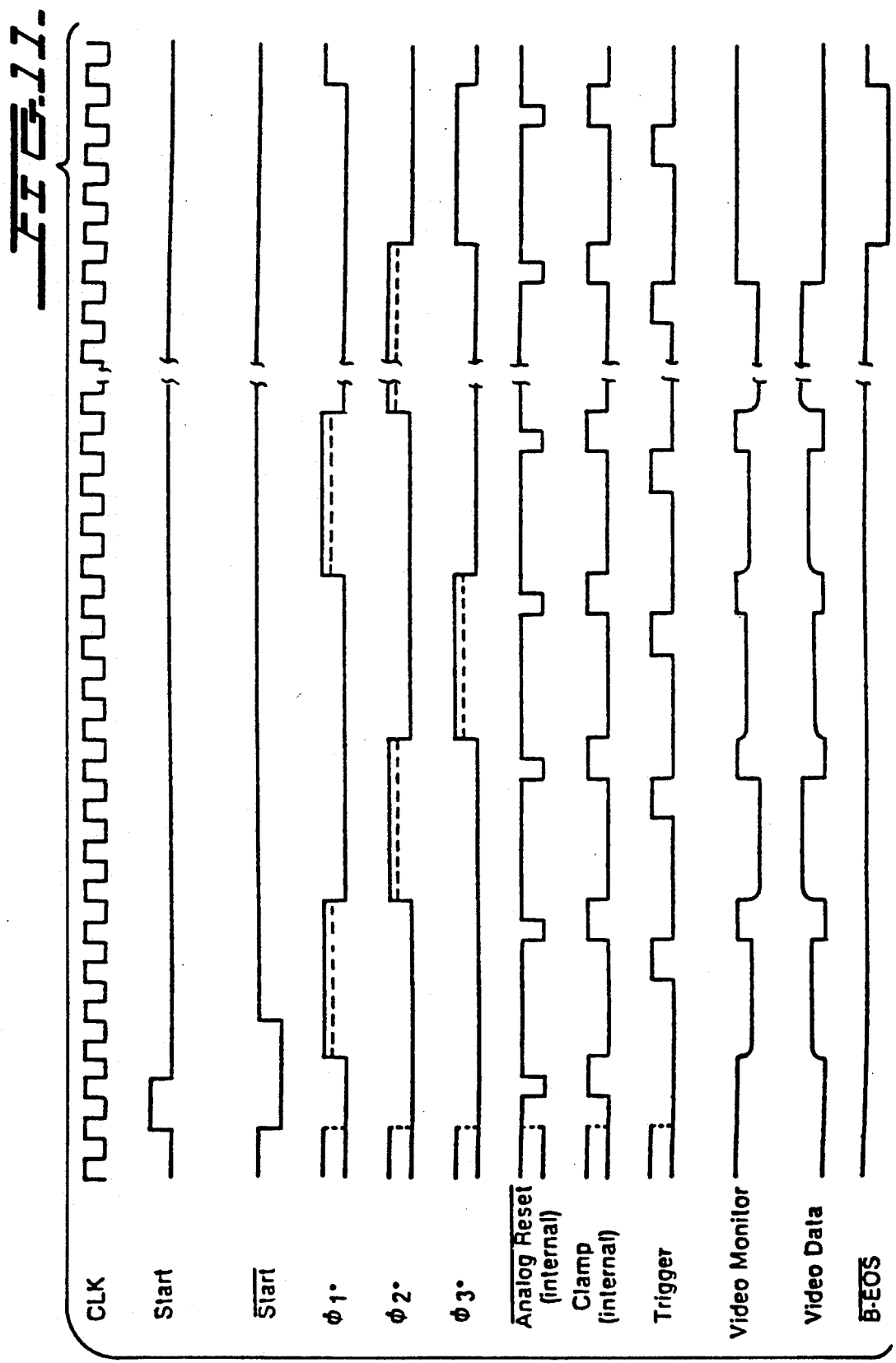
FIG. 11 shows the timing sequence for the driver/amplifier circuitry.
Figure 12:
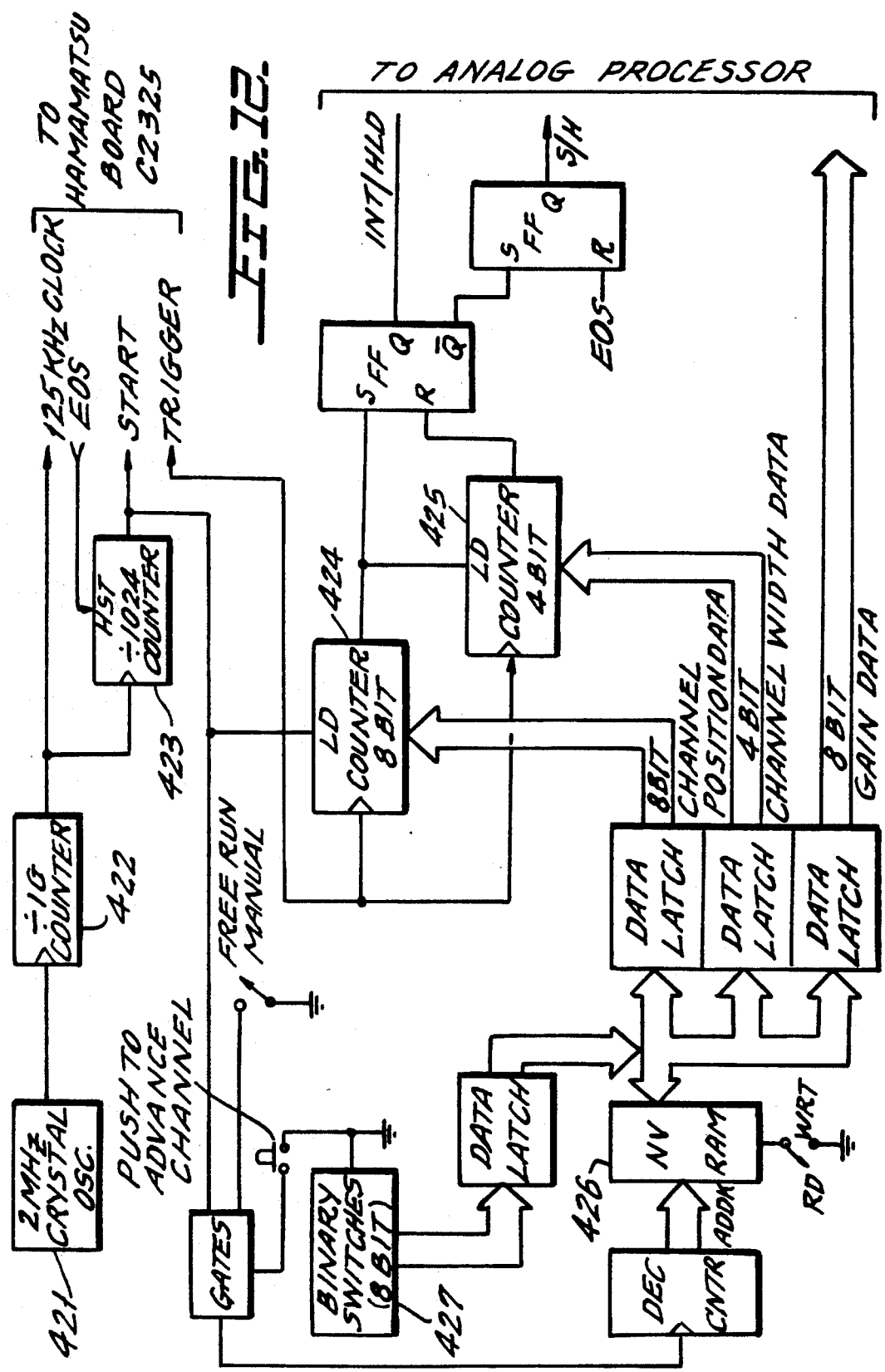
FIG. 12 is a block diagram of the controller/memory circuitry.

The driver/amplifier board 410 is available from HAMAMATSU (C2325), and generates all the necessary control signals (3φ clock and START) shown in the timing diagram of FIG. 11, wherein solid lines represent "PCD-OFF", broken lines represent "PCD-ON", the pulse width of a three phase clock "$\phi_1, \phi_2, \phi_3$" is 4 times that of the "CLK" period, and B-EOS is obtained from $\phi_2$. Board 40 also contains a charge integrator and amplifiers (FIG. 10) so that a voltage output (6 V maximum) is available serially from the board. The overall gain at the "Video Data" output is $3 \times 10^{11}$ V/coulomb. The board requires an external clock and a start pulse which are provided by the controller board 420 with the circuitry shown at the top of FIG. 12. Board 410 also requires ±15 V and ±5 V power supplies.

The controller/memory 420 (shown in detail in FIG. 12) serves three main purposes: (1) to provide the clock and start pulse for the HAMAMATSU driver/amplifier board 410;

(2) to provide all the control signals for the analog processor 430; and (3) to store all the wavelength calibration data and channel gain/offset data on an NV (nonvolatile) RAM 426.

A 125 kHz clock required by the array driver 410 is derived from a 2 MHz crystal 421 and a binary counter divider 422. Since the array driver requires four clock pulses to scan one element to the next, each element on the spatial domain corresponds to 32 μs in the time domain. A start pulse is generated after every 1028 clock pulses thru a 14 bit counter divider circuit 425. The rest of the controller functions are implemented mostly with programmable counters 424, 425, the data input to which are supplied by the NV RAM 426.

Each wavelength channel has two sets of data, first the starting element ($N_S$) and second, the number of elements (ΔN) included in the channel. The first number corresponds to the position and the second corresponds to the bandwidth of the channel on the detector array. Table II below shows the channel numbers and the corresponding position and width data.

TABLE II

| | Wavelength Channel Data | | | | |
|---|---|---|---|---|---|
| | Wavelength | Element # | | Binary Data | |
| Channel # | range nm | $N_s$ | ΔN | $N_s$ | ΔN |
| 1 | 327 to 353 | 1st | 18 | 00000001 | 010010 |
| 2* | 393 to 407 | 45th | 10 | 00101101 | 001010 |
| 3** | 433 to 439 | 72nd | 4 | 01001000 | 000100 |
| 4 | 449 to 471 | 83rd | 15 | 01010011 | 001111 |
| 5 | 495 to 505 | 114th | 7 | 01110010 | 000111 |
| 6* | 530 to 550 | 138th | 14 | 10001010 | 001110 |
| 7 | 594 to 606 | 183rd | 9 | 01110111 | 001001 |
| 8 | 624 to 636 | 204th | 8 | 01001100 | 001000 |
| 9 | 666 to 674 | 234th | 6 | 11101010 | 000110 |
| 10 | 674 to 686 | 241st | 7 | 11110001 | 000111 |

**Primary wavelength calibration channel from low pressure mercury lamp
*Secondary wavelength calibration channel from low pressure mercury lamp These data are written into the wavelength decoding NV RAM 426 manually with 8-bit binary switches 427. These data are loaded automatically into the wavelength counters 424, 425 that generate integrate/hold (INT/HLD) pulse required by the integrator of the analog processor 430.

The INT/HLD pulse starts $N_S \times 32$ μs after the start (STRT) pulse and stays ON for ΔN×32 μs. The complement of INT/HLD is also supplied to analog processor 430.

The channel can be switched from one to another either manually (with a momentary toggle switch), or automatically by a counter which is clocked by the STRT pulse continually. The channel data are changed whenever the detector array 400 is moved.

The controller 420 also generates a sample/hold (S/H) signal for the analog processor. This signal is derived from the INT/HLD by a flipflop which is reset by an end of scan (EOS) pulse from the array driver board.

Figure 13:
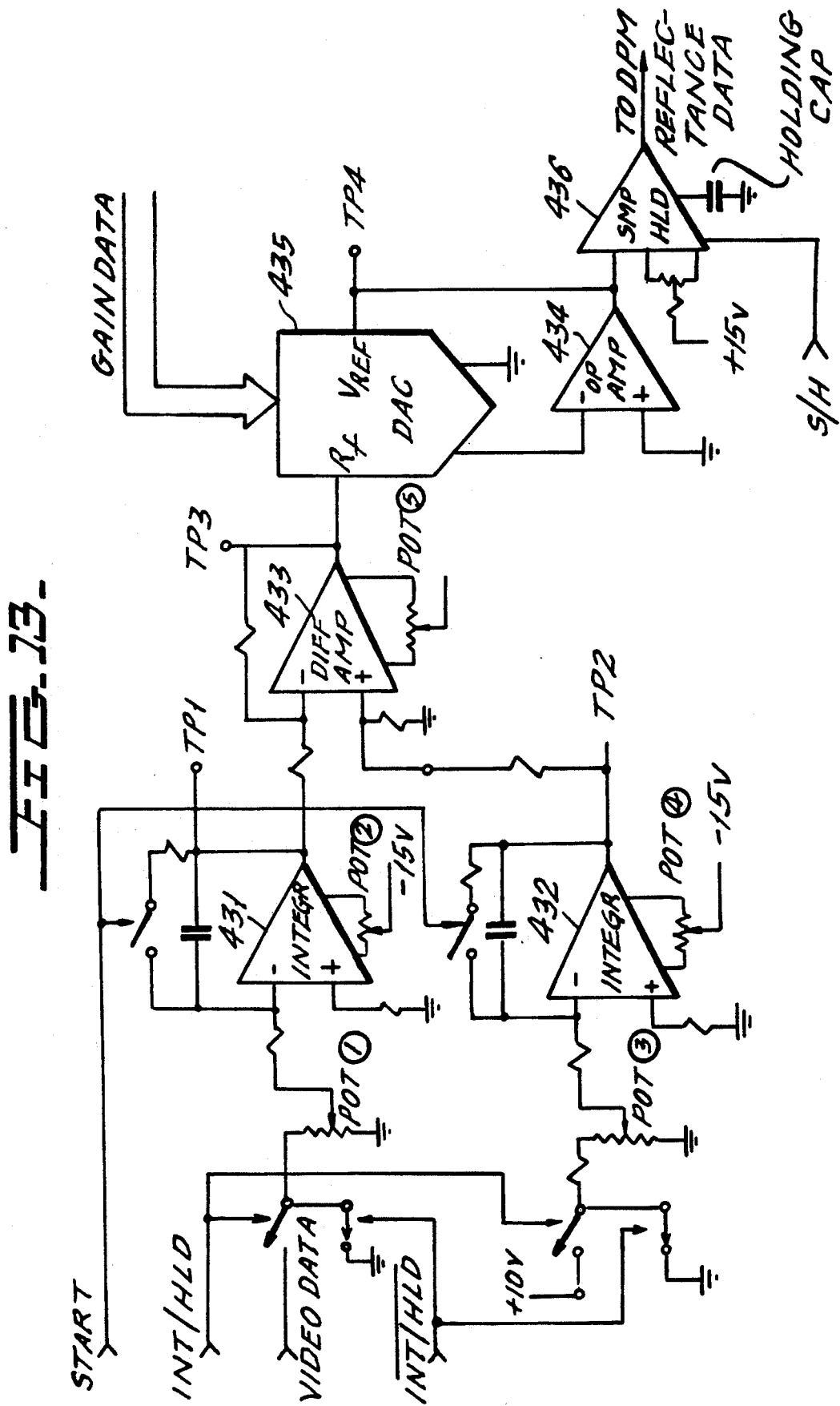
FIG. 13 shows the analog processor circuitry.

The analog processor 430, as illustrated in detail in FIG. 13, has three major functions:

(1) integration (summation) of the detector outputs within a given wavelength channel;

(2) introduce digitally controlled gain and offset adjustments at different wavelength channels; and (3) sample and hold the analog data for a digital panel meter (DPM) for analog to digital (A/D) conversion.

Figure 14:
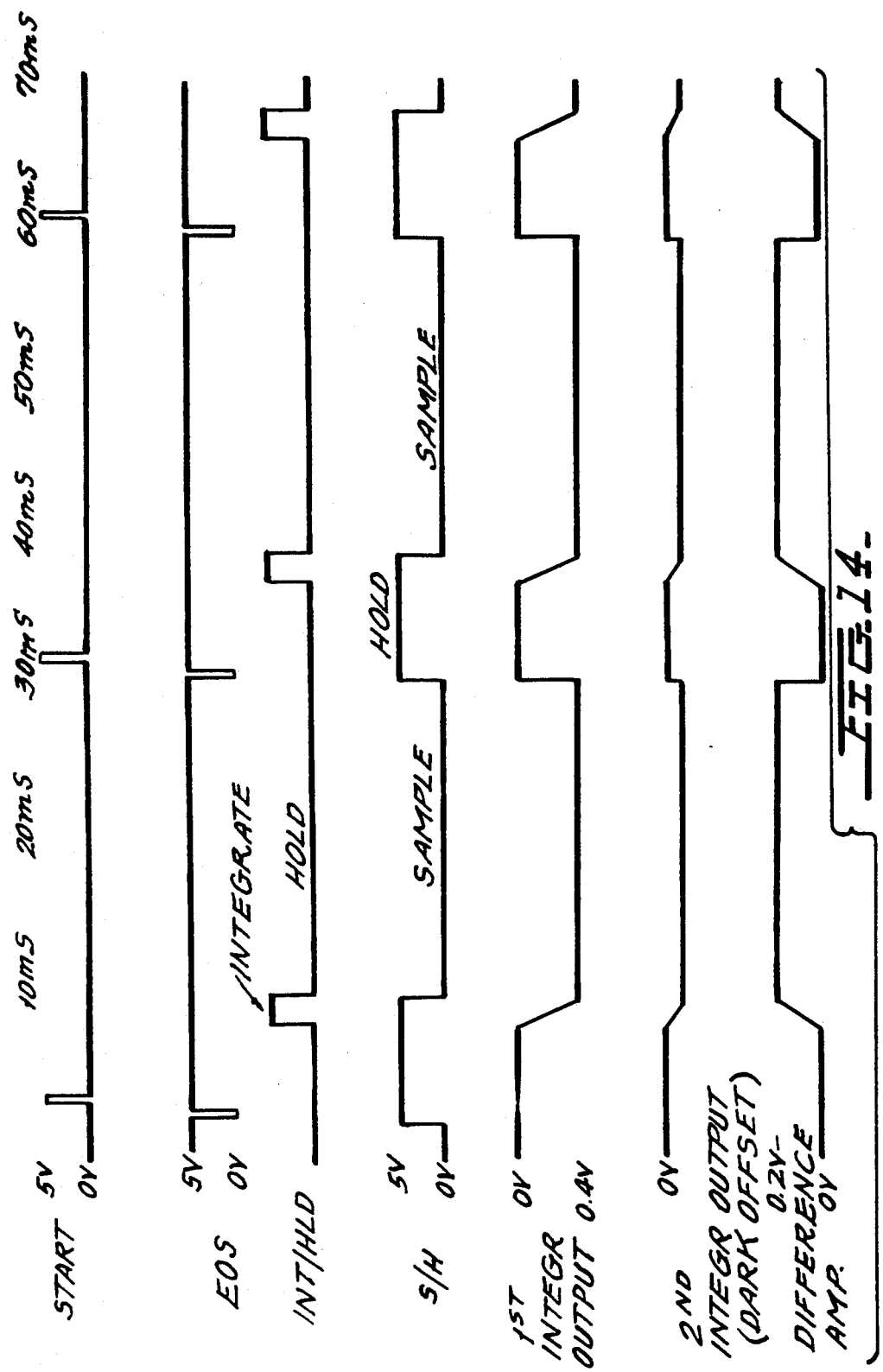
FIG. 14 shows the timing sequence for the integration operation performed by the analog processor.

The integrator 431 integrates the video output from the array driver board only during the period when INT/HLD signal is high and holds the integrated value until it is reset by the next STRT pulse as shown in the timing diagram of FIG. 14. Since the duration of the INT/HLD signal is directly proportional to the wavelength bandwidth (also the number of elements of the array) in a given channel, the integrator output is proportional to the integral of reflectance with respect to wavelength within the range of the given channel. A second identical integrator 432 integrates and holds the dark output of the detectors during the same period. The two integrated and held outputs are then fed to a difference amplifier 433. The output of amplifier 433 is, therefore, free of offset error due to dark current.

The output of the difference amplifier 433 goes to a digitally controlled gain amplifier, which is implemented with an op-amp 434 with a multiplying 8-bit digital to analog converter 435 (DAC) placed in the feedback loop. The gain of the amplifier is thus, 255/D, where D is the digital input (decimal equivalent). The digital input comes from NV RAM 426, where gain data has been written into manually with binary switches 427 at specific channel addresses. The gain data are obtained by normalizing all the channel outputs at 5 V when a reference slide is held at the view port. The final analog output is sample and held (by SMP/HLD 436) before being converted to digital data. SMP/HLD 436 samples only while the integrator 431 is holding the integrated output and holds while the integrator 431 is integrating.

Analog to digital (A/D) conversion takes place in a 4½ digit digital panel meter 440 (FIG. 9) from DATEL. The converter is a dual slope integrating type with a conversion rate of up to 3 per second with a resolution of 100 $\mu$V ($\pm$2 counts on a 16-bit counter).

EXAMPLE

The reflectometer was tested with an UV source with known spectral lines. Once the array and grating were positioned and aligned with respect to the 436 nm line, the other spectral lines (there are five lines in the whole wavelength range) could be identified to within $\pm$1.5 nm.

The instrument readings were normalized with a standard white slide by setting the gains at different channels so that the DPM output reading was 3.0000 volts for all the wavelength channels. These gain settings were stored in the NV RAM 426. Different colored slides (stained with red, yellow, green and blue marker pens) were then tested. As expected, the tests showed peaks at around 660 nm for red, at around 630 nm for yellow, at around 550 nm for green and at around 450 nm for blue.

Although the present invention has been described in connection with a preferred embodiment thereof, many other variations and modifications will now become apparent to those skilled in the art without departing from the scope of the invention. It is preferred, therefore, that the present invention not be limited by the specific disclosure herein, but only by the appended claims.

What is claimed is:

1. A system for measuring the absorption of light by a sample in selected regions of the light spectrum, comprising:

means for illuminating the sample;

a fixed fiber optic collector for directly collecting diffusely reflected energy from the sample, the optical fibers forming said collector being generally straight and short in order to control loss of the reflected light, the optical fibers being grouped in a bundle and extending from an entrance end that is generally circular to an exit end that is arranged in the shape of a rectangular slit, said entrance end being disposed immediately adjacent the sample so that said fibers each receive and transmits light from the entire sample, and said entrance end of each of said fibers in said bundle having an acceptance angle that is at least as large as the associated optical exit angle of each of said fibers;

a holographic, concave diffraction grating for dispersing the reflected energy projected onto it through the slit of the collector into its component wavelengths on a flat spectral plane, said light transmitted by each of said fibers of said collector filling said grating;

a photodetector array comprising a plurality of photodetectors located at the spectral plane for detecting the separated energy at its various wavelengths; and means for processing electrical signals generated by said photodetectors corresponding to the presence of light at the various wavelengths to obtain numerical data corresponding to a reflectance value within a wavelength bandwidth.

2. The system of claim 1, wherein the means for illuminating the sample comprises:

a halogen lamp having a filament;

a dichroic spherical mirror disposed behind the lamp; and a lens system disposed in front of the lamp and the mirror for producing a superimposed, three-dimensional image of an uninterrupted array of glowing filaments on the sample.

3. The system of claim 1, wherein the collector comprises a glass fiber optic bundle.

4. The system of claim 3, wherein the bundle has end portions which are rigid and are not secured in the middle portion.

5. The system of claim 1, wherein the rectangular slit comprises at least two rows of optical fibers of the collector.

6. The system of claim 1, wherein the grating has about 200 to 600 grooves/mm.

7. The system of claim 1, wherein the grating has a radius of curvature of about 40 to 200 mm.

8. The system of claim 1, wherein the grating has a radius of curvature of about 100 mm.

9. The system of claim 1, wherein the means for illuminating the sample is oriented at an angle with respect to the plane of said sample.

10. The system of claim 9, wherein the angle of illumination is about 45°.

11. The system of claim 2, wherein the image projected on said sample has a round shape.

12. A method for measuring the absorption of light by a sample in selected regions of the light spectrum, comprising the steps:

illuminating the sample with light from a light source;

collecting optical energy reflected from the sample directly in a fixed fiber optic collector formed of short, generally straight fibers, the optical fibers being grouped in a bundle and extending from an entrance end that is generally circular to an exit end that is arranged in the shape of a rectangular slit projecting the reflected energy passing through the rectangular slit onto a holographic, concave diffraction grating;

said collecting at each fiber entrance end adjacent said sample being from the entire sample and said projecting at each said fiber slit end filling said grating, the entrance angle over which said collecting occurs at each fiber being at least as great as the exit angle over which said projecting occurs at each said slit end;

separating the reflected energy into its component wavelengths on a flat spectral plane by reflecting the energy off the grating; and detecting the separated energy.

13. The method of claim 12, wherein the step of detecting the separated energy comprises projecting the separated energy onto a photodetector array.

14. The method of claim 13, further comprising the step of processing electrical signals generated by the photodiode array to obtain numerical data corresponding to a reflectance value within a wavelength bandwith.

* * * * *